United States Patent [19]

Frank-Neumann et al.

[11] Patent Number: 4,677,218
[45] Date of Patent: Jun. 30, 1987

[54] CYCLOPROPANE DERIVATIVES CONTAINING THE THIOCARBONATE GROUP

[75] Inventors: Michel Frank-Neumann, Strasbourg; Madjid Sedrati, Osthoffen; Jean-Pierre Vigneron, Boissy-Sous-Saint-Yon; Vincente Bloy, Paris, all of France

[73] Assignee: Roussel Uclaf, Paris, France

[21] Appl. No.: 755,486

[22] Filed: Jul. 16, 1985

Related U.S. Application Data

[62] Division of Ser. No. 632,203, Jul. 18, 1984, Pat. No. 4,551,545.

[30] Foreign Application Priority Data

Jul. 21, 1984 [FR] France ............................... 83 12073

[51] Int. Cl.[4] .......................................... C07C 154/00
[52] U.S. Cl. ................................................. 558/243
[58] Field of Search ..................................... 558/243

[56] References Cited

U.S. PATENT DOCUMENTS 3,864,376  2/1975  Henrick et al. ..................... 558/243

FOREIGN PATENT DOCUMENTS 2639777  9/1976  Fed. Rep. of Germany ...... 558/243
2085428  4/1982  United Kingdom ................ 558/243

OTHER PUBLICATIONS

Majewski et al., J. Org. Chem., 1984, 49, 2682–2687.
Gerlach et al., J. C. S. Chem. Comm., 1972, pp. 1215–1216.
Majewski et al., Tetrahedron Letters, vol. 23, #13, pp. 1343–1346.

*Primary Examiner*—John M. Ford
*Assistant Examiner*—Robert C. Whittenbaugh
*Attorney, Agent, or Firm*—Bierman & Muserlian

[57] ABSTRACT

A process for the preparation of racemic or optically active isomers of alkyl esters of cis chrysanthemic of the formula

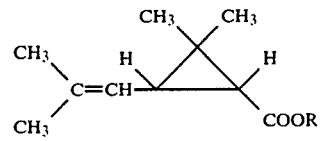

wherein R is alkyl of 1 to 6 carbon atoms comprising reacting a racemic or optically active cis compound of the formula

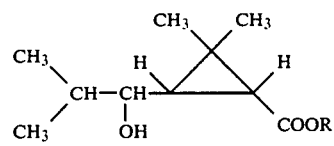

wherein R has the above definition with an aryl halothioformate of the formula

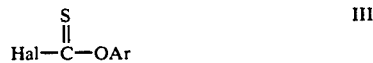

wherein Hal is a halogen and Ar is aryl of 6 to 12 carbon atoms optionally substituted with at least one alkyl of 1 to 3 carbon atoms to obtain a compound of the formula

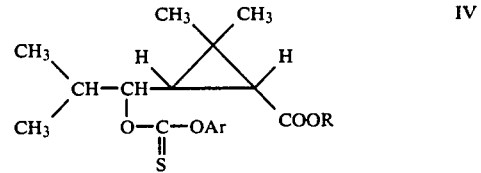

of cis configuration and heating the latter optionally in an organic solvent to obtain the compound of formula I and novel intermediates.

1 Claim, No Drawings

CYCLOPROPANE DERIVATIVES CONTAINING THE THIOCARBONATE GROUP

PRIOR APPLICATION

This application is a division of copending U.S. patent application Ser. No. 632,203 filed July 18, 1984, now U.S. Pat. No. 4,551,545.

STATE OF THE ART

Majewski et al [Tetrahedron Letters, Vol. 23, No. 13, p. 1343–1346 (1982)] describe a route to a pyrethroid amide by a base-induced epoxyamide cyclization. Gerlach et al [J.C.S. Chem. Comm., 1972, p. 1215–1216] describe acylation of sterically hundered alcohols with 0–4-methylphenyl chlorothioformate. Published British application No. 2,085,428 describes forming a 3-vinyl side chain on cyclopropane carboxylates by reacting the corresponding 1-hydroxyethyl substituted compound with a phosphine. Also pertinent is DE-OS 2,639,777.

OBJECTS OF THE INVENTION

It is an object of the invention to provide a novel process for the preparation of alkyl esters of cis chrysanthemic acid.

It is another object of the invention to provide novel intermediate products.

These and other objects and advantages of the invention will become obvious from the following detailed description.

THE INVENTION

The novel process of the invention for the preparation of racemic or optically active isomers of alkyl esters of cis chrysanthemic of the formula

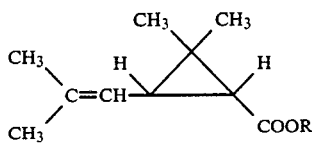

I wherein R is alkyl of 1 to 6 carbon atoms comprises reacting a racemic or optically active cis compound of the formula

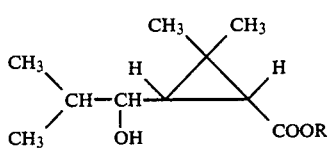

II wherein R has the above definition with an aryl halothioformate of the formula

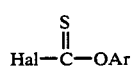

III wherein Hal is a halogen and Ar is aryl of 6 to 12 carbon atoms optionally substituted with at least one alkyl of 1 to 3 carbon atoms to obtain a compound of the formula

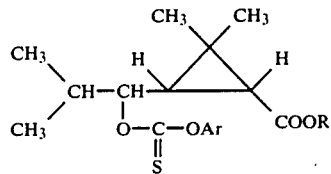

IV of cis configuration and heating the latter optionally in an organic solvent to obtain the compound of formula I.

Examples of R are alkyl such as methyl, ethyl, propyl, isopropyl and linear and branched butyl, pentyl and hexyl.

In formula III, Hal is preferably chlorine but may be other halogens and Ar is preferably phenyl or naphthyl optionally substituted with at least one alkyl of 1 to 3 carbon atoms such as methyl or ethyl. The preferred compound of formula III is p-tolyl chlorothioformate.

In a preferred mode of the process, the compound of formula IV is heated at 100° to 150° C. in a non-polar, organic solvent, preferably a dichlorobenzene or trichlorobenzene. The heating can also be performed in the absence of a solvent. The compounds of formula II are known from Agr. Bio. Chem., Vol. 28 (7), p 456-4-6 (1964).

A facet of the invention involves a process for the preparation of the racemic mixture or optically active compounds of formula II of cis configuration comprising reacting a racemic or optically active compound of the formula

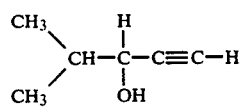

V with a carbonating reagent to obtain a compound of the formula

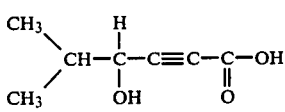

VI subjecting the latter to a selective reduction to obtain a compound of the formula

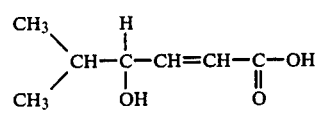

VII cyclizing the latter to obtain a lactone of the formula

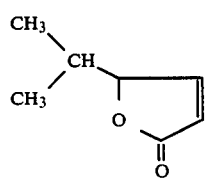

VIII reacting the latter with diazo-2-propane to obtain a mixture of pyrazolines of the formulae

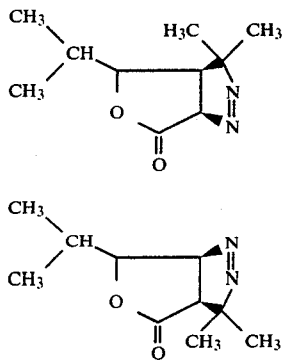

which, optionally separating the mixture and submitting the compound of formula IX$_a$ or the compound of formula IX$_b$ or their mixture to irradiation in the presence of a sensitizer to obtain a compound of the formula

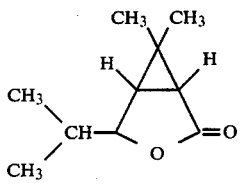

and treating the latter with a basic agent and then with an esterification agent to obtain the corresponding compound of formula II.

In a preferred mode of the latter process, the carbonation of the compound is effected with carbonic acid gas in the presence of a strong base such as a lithium alkyl and the reduction of the compound of formula VI is preferably effected with hydrogen in the presence of a catalyst. The cyclization of the compound of formula VII is either effected spontaneously or in the presence of an acid, preferably a mineral acid. The irradiation step may be effected with a mercury vapor lamp in the presence of a sensitizer such as benzophenone. The treatment of a compound of formula X is effected with a basic agent such as sodium hydroxide or preferably potassium hydroxide in an aqueous-alcohol solvent and the esterification may be effected in situ without isolution of the acid.

The esterification agent leading to the compounds of formula II can be any reagent known to an expert to obtain the desired esters. When it is desired to prepare a methyl ester, it is particularly convenient to use diazomethane. When it is desired to prepare other alkyl esters, the corresponding diazoalkanes can be used.

The synthesis of cis chrysanthemic acids and their alkyl esters offers at the present time a quite particular interest, because they are used especially for the preparation of cyclopropane carboxylic acids with a dihalovinyl chain, certain esters of which are well known to possess a remarkable pesticidal activity, in particular insecticidal. The invention process provides a total synthesis of racemic or optically active alkyl esters of cis chrysanthemic acid, comprising a small number of steps with high yields. This synthesis is stereo-specific and in fact, the addition reaction and the cyclization leading to the pyrazolines of formulae IX$_a$ and IX$_b$ are stereo-specific, and the following stages do not cause any isomerization.

The compound of formula II, and then the compounds of formulae IV and I of cis configuration are the only isomers obtained. Furthermore, the process of the invention presents a quite unexpected character in the light of the teaching of prior art. In fact, many authors, among them Matsui et al Agr. Biol. Chem. 28 456 (1964), Ficini et al Tet. Letters, 1976, 2441 and Snieckus et al Tet. Letters, 1982, 1343, did not succeed in dehydrating the cis configuration alcohol of formula II. The process of the present invention enables this dehydration to be effected with a total yield which can exceed 70%.

The racemic or optically active compound of formula V utilized as a starting material is known and described, for example, in Tet. Letters No. 29, p. 2683 (1979).

The novel intermediates of the invention are the racemic and optically active compounds of formula IV, VI, VII, IX$_a$ and IX$_b$.

In the following examples there are described several preferred embodiments to illustrate the invention. However, it should be understood that the invention is not intended to be limited to the specific embodiments.

EXAMPLE 1

(1S,cis) methyl chrysanthemate

STEP A: 4R-hydroxy-5-methyl-hex-2-ynoic acid 195.6 ml of a 1.3M solution of butyl-lithium in hexane were added slowly to a solution of 10.5 g of 3R-hydroxy-4-methyl-pent-2-yne in 180 ml of tetrahydrofuran cooled to $-78°$ C. and when the addition was finished, an excess of solid carbon dioxide was added in small pieces. An abundant precipitate formed and after returning to ambient temperature, 100 ml of water were added to dissolve the colloidal mass. The aqueous phase after separation from the organic phase was acidified with concentrated hydrochloric acid and was extracted with ether. The solvent is evaporated to obtain 21.05 g of 4R-hydroxy-5-methyl-hex-2-ynolic acid which was crystallized from benzene to obtain 8.9 g of the product in the form of white crystals melting at 80° C. and a specific rotation of $[\alpha]_D^{20} = +10.6°$ (c=2% in dioxane).

STEP B: 5R-Isopropyl-2-(5H)-furanone

A solution of 7.62 g of the product of Step A in 120 ml of methanol was hydrogenated at ordinary temperature and pressure in the presence of 500 mg of palladium on barium sulfate and a few drops of quinoline and the hydrogenation was stopped when the theoretical quantity of hydrogen was consumed. The catalyst was filtered off and the filtrate was evaporated to dryness. The residue was dissolved in 20 ml of ether, and to this solution 2 ml of concentrated HCl were added. The mixture was vigourously stirred and the ethereal phase was decanted, washed with sodium bicarbonate and with water. After drying over sodium sulfate, the ether was evaporated and the residue was distilled to obtain 5.70 g of 5R-isopropyl-2-(5H)-furanone with a boiling point of 78°–79° C. at 0.1 mm. mercury and having a specific rotation of $[\alpha]_D^{25} = -96°$ C. (c=2% in dioxane).

STEP C:
4,4-dimethyl-6R-isopropyl-7-oxa-2,3-diazabicyclo-oct-2-en-8-one (compound A) and
4,4-dimethyl-8R-isopropyl-7-oxa-2,3-diazabicyclo-oct-2-en-6-one (compound B)

25 ml of a 3.3M solution of diazo-2-propane in an ether ethylbenzene mixture prepared according to Dietrich-Buchecker et al (Tetrahedron, Vol. 33 p. 745 (1977) were added in 5 ml portions to a solution of 20 ml of ether and 5.30 g of the product of Step B, while the temperature was kept at about $-10°$ C. After 2 hours at ambient temperature, the ether was evaporated at ambient temperature and the residue was chromatographed over silica gel. Elution with hexane with 20% of ether yielded a first fraction of compound B which was crystallized (m.p. 78°–82° C. with decomposition) followed by 300 mg of a mixture of compounds A and B, and a final fraction of 4.37 g of compound A in the form of a colorless liquid.

STEP D: (1S,3R,4R)
6,6-dimethyl-4-isopropyl-3-oxabicyclohexan-2-one

A solution of 2.38 g of compound B of Step C and 4.8 g of benzophenone in 200 ml of benzene was irradiated with a mercury vapor lamp type Philips HPK125 until the stochiometric quantity of nitrogen had been given off. After evaporation of the solvent, the residue was chromatographed over silica gel and eluted with hexane with 20% of ether to obtain 1.28 g of (1S,3R,4R) 6,6-dimethyl-4-isopropyl-3-oxabicyclo-hexan-2-one having a specific rotation of $[\alpha]_D^{20}= +80°$ (chloroform).

Photolysis under the same conditions of 4.30 g of compound A in the presence of 9.0 g of benzophenone in solution in 1 liter of benzene and after total evolution of the nitrogen and isolation as previously, 3.30 g of the same cyclopropane lactone as above were obtained with a specific rotation of $[\alpha]_D^{20}= +70°$ (chloroform).

STEP E: Methyl (1S,3R)
2,2-dimethyl-3-(1-hydroxy-2-methyl)-propyl-1-cyclopropane carboxylate A solution of 4.2 g of the product of Step D in 55 ml of ethanol was mixed with a solution of 11.3 g of potassium hydroxide in 30 ml of water. After 48 hours at ambient temperature and elimination of the greater part of the ethanol under reduced pressure, water was added and the aqueous solution was washed with ether. Then the aqueous phase was acidified with 10% hydrochloric acid, and extracted with ether. The organic extract was dried and then treated immediately with an ethereal solution of diazomethane, slightly in excess. After one hour at ambient temperature, the solvent was evaporated under reduced pressure to obtain 5.0 g of methyl (1S,3R) 2,2-dimethyl-3-(1-hydroxy-2-methyl)-propyl-1-cyclopropane carboxylate which was used as is in the continuation of the synthesis.

STEP F: Methyl (1S,3R)
2,2-dimethyl-3-[1-(4-methyl-phenoxy-carbonothioyloxy)-2-methylpropyl]-1-cyclopropane-carboxylate 2.4 ml of O-paratolyl chlorothioformate were added dropwise to a mixture of 2.80 g of the product of Step E and 1.5 ml of pyridine in 40 ml of methylene chloride. After 48 hours at ambient temperature, the reaction mixture was diluted with 200 ml of ether and was washed with water. After drying and evaporation of the solvents, the residue was chromatographed over silica gel and eluted with hexane with 5% of ether to obtain 2.34 g of methyl (1S,3R) 2,2-dimethyl-3-[1-(4-methyl-phenoxy-carbonothioyloxy)-2-methylpropyl]-1-cyclopropane-carboxylate.

STEP G: Methyl (1S cis) chrysanthemate

A solution of 1.725 g of the product of Step F in 20 ml of 1,2,4-trichloro-benzene was heated slowly to 140° C. and then kept at this temperature for 15 minutes. After cooling, the solution was chromatographed over silica gel and eluted with hexane with 2% of ether to obtain 692 mg of methyl (1S,cis) chrysanthemate having a specific rotation of $[\alpha]_D^{20}= -60.5°$ C. (benzene) of (1S,3R) configuration.

EXAMPLE 2

Methyl (1R,cis) chrysanthemate

Using the procedure of Example 1, 3S-hydroxy-4-methylpent-2-yne was reacted with the same succession of stages to obtain methyl (1R,cis) chrysanthemate having a specific rotation of $[\alpha]_D^{20}= +66.5°$ (benzene).

EXAMPLE 3

Methyl cis chrysanthemate

STAGE A:
4,4-dimethyl-6-isopropyl-7-oxa-2,3-diazabicyclo-oct-2-en-8-one (compound C) and
4,4-dimethyl-8-isopropyl-7-oxa-2,3-diazabicyclo-oct-2-en-6-one (compound D)

40 ml of a 3M solution of diazo-2-propane in an ether-ethylbenzene mixture [prepared according to Dietrich-Buchecker et al Tetrahedron., Vol. 33, p. 745 (1977)] were added in portions of 5 ml to a solution of 7.70 g of 5(RS) isopropyl-2 (5H) furanone obtained as described in Example 1 beginning with 3(RS) hydroxy-4-methylpent-2-yne in 20 ml of ether while keeping the temperature at about $-10°$ C. After 2 hours at ambient temperature, the ether was evaporated at ambient temperature and the residue was chromatographed over silica gel. Elution with hexane with 20% of ether yielded one fraction of 4.45 g of compound D crystallized (m.p. 68°–69° C.) and one fraction of 7.25 g of compound C in the form of a colorless liquid.

STEP B:
6,6-dimethyl-4-isopropyl-3-oxabicyclohexan-2-one

A solution of 3.50 g of the D compound of Step A and of 7.00 g of benzophenone in 1 liter of benzene was irradiated with a mercury vapour lamp of Philips type HPK125 until the stochiometric quantity of nitrogen had evolved. After evaporation of the solvent, the residue was chromatographed over silica gel and eluted with hexane first with 5% and then with 10% of ether to obtain 2.73 g of 6,6-dimethyl-4-isopropyl-3-oxabicyclohexan-2-one with a boiling point of 47°–48° C. at 0.05 mm Hg.

Photolysis under the same conditions of 4.30 g of compound C in the presence of 9.0 g of benzophenone in solution in 1 liter of benzene and after total evolution of nitrogen and separation as previously yielded 3.30 g of the same cyclopropane lactone.

STEP C: Methyl cis 2,2-dimethyl-3-(1-hydroxy-2-methyl)-propyl-1-cyclopropane carboxylate A solution of 2.7 g of the product of Step B in 40 ml of ethanol was mixed with a solution of 7.5 g of potassium hydroxide in 20 ml of water. After 48 hours at ambient temperature and elimination of the greater part of the ethanol under reduced pressure, water was added and the aqueous solution was washed with ether. The aqueous phase was then acidified with 10% hydrochloric acid and was extracted with ether. The organic extract was dried and evaporated to dryness and the residue of 2.9 g was immediately treated with an ethereal solution of diazomethane in slight excess. After one hour at ambient temperature, the solvent was evaporated under reduced pressure to obtain 3.10 g of methyl cis 2,2-dimethyl-3-(1-hydroxy-2-methyl)-propyl-1-cyclopropane carboxylate melting at 58°–59° C. after crystallization from an ethyl ether-hexane mixture.

STEP D: Methyl cis 2,2-dimethyl-3-[1-(4-methyl-phenoxycarbonothioyloxy)-2-methylpropyl]-1-cyclopropane carboxylate 0.3 ml of O-p-tolyl chlorothioformate was added dropwise at 0° C. to a mixture of 0.2 g of the product of Step C and 0.16 ml of pyridine in 6 ml of dry methylene chloride. After 48 hours, the reaction mixture was adsorbed at 0° C. on a minimal quantity of silica (≃2 g) and then was chromatographed over silica gel. Elution with hexane with 2% of ether yielded 0.383 g of methyl cis 2,2-dimethyl-3-[1-(4-methyl-phenoxycarbonothioyloxy)-2-methylpropyl]-1-cyclopropane carboxylate melting at 92°–93° C. after crystallization from hexane.

STEP E: Methyl cis chrysanthemate

A solution of 0.693 g of the product of Step D in 10 ml of 1,2,4-trichloro-benzene was heated slowly at 140° C. and then maintained for fifteen minutes at this temperature. After cooling, the solution was poured directly onto a column of silica gel and eluted with hexane with 2% of ether to obtain 0.323 g of methyl cis-chrysanthemate.

Various modifications of the products and processes of the invention may be made without departing from the spirit or scope thereof and it should be understood that the invention is intended to be limited only as defined in the appended claims.

What we claim is:

1. A compound having a formula selected from the group consisting of

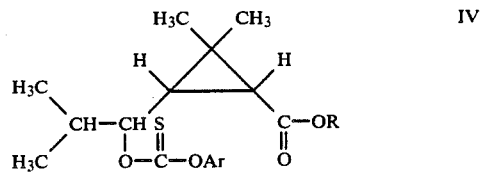

of cis configuration in racemic or optically active form, wherein R is alkyl of 1 to 6 carbon atoms and Ar is is selected from the group consisting of phenyl or naphthyl optionally substituted with at least one alkyl of 1 to 3 carbon atoms.

* * * * *